United States Patent [19]
Kell

[11] Patent Number: 5,955,370
[45] Date of Patent: Sep. 21, 1999

[54] URINE ADULTERATION TEST METHOD

[75] Inventor: Michael Kell, Atlanta, Ga.

[73] Assignee: U.D. Testing, Inc., Gainesville, Ga.

[21] Appl. No.: 08/888,246

[22] Filed: Jul. 7, 1997

Related U.S. Application Data

[63] Continuation-in-part of application No. 08/715,016, Sep. 17, 1996, Pat. No. 5,776,783, which is a continuation-in-part of application No. 08/675,863, Jul. 5, 1996, Pat. No. 5,652,146, which is a division of application No. 08/248,102, May 24, 1994, Pat. No. 5,547,878, which is a continuation-in-part of application No. 08/145,821, Nov. 2, 1993.

[51] Int. Cl.$^6$ .................................................. G01N 33/48
[52] U.S. Cl. ................................. 436/2; 436/111; 436/901
[58] Field of Search .................................. 436/2, 63, 111, 436/808, 901, 171

[56] References Cited

U.S. PATENT DOCUMENTS

| | | |
|---|---|---|
| 2,564,247 | 8/1951 | Carson et al. . |
| 3,856,469 | 12/1974 | Schneider et al. ...................... 234/230 |
| 3,901,655 | 8/1975 | Shukla et al. . |
| 4,104,367 | 8/1978 | Gomez et al. ............................. 424/1 |
| 4,196,185 | 4/1980 | Focella et al. ............................. 424/1 |
| 5,047,329 | 9/1991 | Suzuki ..................................... 435/18 |
| 5,137,692 | 8/1992 | Fritz ........................................ 422/61 |
| 5,179,027 | 1/1993 | Fisher ...................................... 436/56 |
| 5,547,878 | 8/1996 | Kell ........................................ 436/111 |

OTHER PUBLICATIONS

Balabanova, et al, Methadone distribution in blood, cerebrospinal fluid, urine and organ tissues, Embase No. 92091431, Austria 1991.

Nilsson et al, Effect of Urinary pH on the disposition of methadone in man, Embase No. 82171209, W. Germany 1982.

Chimera Research & Chemical, Inc., 1996–1997 Product Catalog, No Date Supplied.

Chimera Research & Chemical, Inc., SG Perfect Urinalysis System Reagent Kits, May 1996.

Prediction of creatinine clearance from plasma creatinine; comparison, M. Robertshaw, K.N. Lai & R Swaminathan, British Journal Clin. Pharmac., 1989, pp. 275–280.

Evaluation of Urine Creatinine as a Marker to Identify Dilute Specimens Being Analyzed for Drugs of Abuse, Barbara Mayer and Gary Hemphill, MRO Alert (Medtox Laboratories, Inc., St. Paul, MN 55112), vol. III No. 6, Aug. 1992, pp. 2–4.

Adulteration of Urine Specimens, John T. Cody, Adapted from Cody JT. Forensic Sci. Rev., 1990, pp. 181–207.

Analytical Toxicology for the MRO, The Medical Review Officer Handbook, No Date Supplied, Chapter Ten, pp. 163–172.

*Primary Examiner*—Lyle A. Alexander
*Attorney, Agent, or Firm*—Kennedy,Davis & Kennedy, P.C.

[57] ABSTRACT

A test method for determining adulteration by diuresis or the addition of a diuretic, which uses creatinine and specific gravity measurements to determine a normalized creatinine value for comparison with expected normalized creatinine values for the substantially diuretic-free population.

10 Claims, 12 Drawing Sheets

URINE ADULTERATION TEST METHOD

REFERENCE TO RELATED APPLICATIONS

This is a continuation-in-part of application Ser. No. 08/715,016, filed Sep. 17, 1996, now U.S. Pat. No. 5,776,783 which is a continuation-in-part of application Ser. No. 08/675,863, filed Jul. 5, 1996, now U.S. Pat. No. 5,652,146 which is a divisional application of application Ser. No. 08/248,102, filed May 24, 1994, now U.S. Pat. No. 5,547,878, issued Aug. 20, 1996, which was a continuation-in-part of application Ser. No. 08/145,821, filed Nov. 2, 1993.

TECHNICAL FIELD

The present invention relates generally to methods of testing urine samples for intentional urine adulteration. More particularly, the invention relates to methods of detecting urine adulteration resulting from the ingestion of diuretic substances, diuresis and by urine substitution.

BACKGROUND OF THE INVENTION

As a result of widespread use of illegal drugs in our society, employers and government agencies have initiated regular drug testing programs which subject potential employees to urine analysis prior to their employment. Such drug testing has become commonplace in the work force, such as the Federal National Institute of Drug Testing (NIDA) program. Often an employer's decision to hire a particular applicant is dependent on the individual passing such a test.

These drug tests are most commonly performed at a laboratory or lab collection site. The most common urine drug tests used today by employers check for the presence of illegal drugs or their metabolites, at certain concentration levels. Drug metabolites are the chemical derivatives of a drug after the drug has been metabolized by the body. For instance, it is not uncommon for employers to test for the presence of the marijuana THC metabolite and the cocaine metabolite in addition to marijuana and cocaine, by using either blood or urine analysis. It should be recognized that urinalysis is clearly preferred by employers and laboratories due to its lower costs, lack of invasiveness for the test subjects, and reduced health risks. If a tested individual has less than a predefined concentration (or cutoff level) of the illegal substance in their urine sample, the drug test result is "negative", and the individual passes the test. If the concentration of the substance in the sample is higher than the cutoff value, the result is "positive" and the individual fails the test.

While such drug testing has curbed some use of illegal substances in the work place, many individuals continue to use these drugs despite the possible physiological and social consequences. These individuals often attempt to adulterate their urine specimens during the test procedure, adulteration being the altering by a patient of his or her urine in an effort to prevent detection of an illicit drug in the urine specimen. This type of activity takes many forms and is often successful in affecting the outcome of drug tests, thereby creating a "false negative" result.

The scientific literature has documented at least two different types of adulteration activities. The first type of activity occurs at the drug testing site and is directed to altering the test result by changing the actual urine sample in some fashion. This activity includes adding a foreign substance directly to the urine sample while it is in a specimen container, such as water, bleach, vinegar or a chemical agent; or substituting a foreign urine specimen for that of the person being tested. The addition of these substances can have a direct effect on the drug test chemical analysis and hence the result. It has been demonstrated that while such activity may be effective in altering the outcome of a drug test, such activity can either be discovered or discouraged through close supervision at the test site or by visual inspection of the urine specimen itself. Often the addition of foreign substances to a specimen alters the appearance and characteristics of the urine. If an individual attempts to substitute a foreign specimen for his/her own, a temperature analysis often tips the test taker off to the scheme. If an individual adds a foreign substance to the specimen, a change in color, clarity, odor, temperature, or pH will indicate the addition of the foreign substance.

The second type of adulteration activity involves the indirect addition of a foreign substance into the urine via ingestion prior to giving the urine sample. The substance ingested is eliminated in the urine sample along with the normal body waste and can have a direct effect on the drug test chemical analysis. This type of adulteration is often more difficult to detect and address because the urine appears normal. The temperature and color of the specimen are within an acceptable range. Examples of this type of activity include drinking large quantities of water prior to taking a urine test or ingesting a naturally derived or manmade chemical compound that affects testing analysis.

By drinking large quantities of water prior to testing, an individual effectively dilutes the concentration of any drug appearing in their urine, potentially lowering the drug concentration below the detectable cutoff level. In this regard, it is important to note that the relative concentration of metabolites in urine is a function of detection time. By hydrating oneself prior to taking a drug test, the amount of drug metabolites in urine is necessarily decreased. However, the amounts of substances in the urine normally produced through the elimination of waste are found even in the hydrated sample, at the same ratio that they would be expected to be found if the kidneys were functioning normally. This is significant since drug tests have a specific cut-off value which indicate a positive or negative result. The effect of drinking large quantities of water (or diuresis) can cause dilution of a urine sample up to ten-fold, which, depending on the concentration of the drug could lead to a false negative result. However, the other substances in urine will still be found in their normal percentages for the amount of water passing through the kidneys.

Essentially, in diuresis, the concentration of drug metabolites for the amount of volume of urine produced can fall below the cut-off value, which can create a false negative result. For example, the drug cutoff level for a particular drug metabolite may be 100 mg/ml. If the urine is diluted down 2–4 times (and the individual had the cut-off level of metabolites in their system before dilution), the individual will appear to pass the test, even though the individual in fact has enough drug in their system to normally fail a drug test. This false negative could then lead to the inappropriate step of hiring the individual. It should be noted however, that sometimes an individual who has drank large quantities of water prior to testing produces a urine which is so dilute that it resembles water in appearance. In this scenario, a drug testing center can reconstruct the particular circumstances by which the individual diluted the sample.

Alternatively, individuals may take diuretics such as water pills to dilute their urine specimen. While the drinking of excessive fluid often results in increased urine from an individual, the water which passes through the individual's kidneys is filtered at the normal rate. In contrast, a diuretic forces greater amounts of fluid from individual cells in the body through the kidneys, resulting in an increased amount of water in the urine sample without a corresponding amount of secondary elements present. In this situation, the ratio of fluid to the amount of secondary substances normally present in the urine would be artificially high. The diuretic effectively dilutes the concentration of illegal substances, but without the need to drink excessive amounts of fluid. While diuretics do not interfere with the chemical mechanics of the drug test, they do have the capability of diluting the concentration of the drug to a level which is either not detectable or is below the established administrative cut-off levels. Some diuretics are very potent and fast acting, lasting for many hours. These can be used to cause significant dilution of the drug in the urine in a very short time period.

As a result of these types of activities, laboratory tests have been developed to determine if urine has been adulterated by dilution. Several properties of the urine are measured in these tests to evaluate whether the urine is adulterated in this manner. Such include testing the amount of ions in the urine (ionic strength), since urine typically includes large amounts of ions, or testing the conductivity of urine, since urine is typically comprised of large amounts of electrically charged particles (ions). Additional tests include pH testing, since urine normally has a narrow pH range, testing the creatinine concentration of the urine, since the body normally eliminates a predictable amount of creatinine, and specific gravity testing, since the body normally eliminates a predictable quantity of solids through the urine.

For example, when checking urine pH, pH is measured as with the use of a pH data/logger-type meter available from Oakton, to see if the urine specimen has a pH within the normally expected pH range of 4.5 to 8.5. Alternatively, pH may be measured through chemical analysis. Chemical pH test methods, exemplified by the pHPERFECT™ test of Chimera Research & Chemical, Inc., is based on the indicator principle which gives a broad range of color intensity covering the entire urinary pH range.

Urine specific gravity (SG) may be measured by methods such as refractometry or by ionic strength in order to determine if it is in the normal range. Ionic strength/specific gravity tests may also be through chemical methods such as sGPERFECT™, also from Chimera, but based on the pKa change of pretreated polyelectrolytes in response to ionic concentration of the test sample. The reaction produces a color change with increasing concentration of the sample.

Creatinine levels may be measured by a creatinine analyzer such as the TDx REA Creatinine System available from Abbott Laboratories to determine if it is in the normal range or through a chemical test such as CR PERFECT™, also from Chimera. Of the various measures however, urinary creatinine level is generally the most useful indicator as to whether a spot sample is that of the patient or of someone else, providing comparative historical data has already been developed for the particular individual.

Once pH, specific gravity, and creatinine level values for the spot urine sample are obtained for a particular individual, comparisons can be made between the sample in question and values previously measured if already available, or in the alternative, comparisons may be made between the sample and a range of established values for a normal testing population. If the test results fall within the acceptable range, the sample is determined to be unadulterated.

It should be noted that the chemical tests commercially available from companies such as Chimera are intended for use as screening tools for determining abnormally high or low urine SG values (based on the presence of ions in the urine) outside the ranges of 1.003 and 1.030 for use with the Olympus, Hitachi, Monarch and other automated systems. Such drug tests are particularly effective in detecting abnormally high specific gravity values if those values are based on increased ions in the urine resulting from certain diuretic use (such as from water pills). Specific chemical testing kits such as the sGPERFECT have different test ranges to determine specific ranges of SG values. Such tests have limited practical value as they are range specific, and often fail to tag adulterated urine specimens with normal specific gravity values.

Furthermore, while the current test methods of urine adulteration are somewhat effective, there are times when the standard ionic strength, pH, and creatinine tests fail to detect urine adulteration by exogenous or endogenous diuretics. Exogenous diuretics are substances which are added to the body either through ingestion or a medical procedure which add solids to the urine that are not detected by ionically-dependent chemical-based specific gravity tests. Urine specific gravity appears normal under these tests. Examples of such substances include iodine from contrast, radiopaque dyes from diagnostic medical procedures, and the osmotic diuretic isosorbide which deposits non-ionic solids in the urine. Endogenous diuretics are substances which function as diuretics but are naturally excreted from the body as a result of an abnormal medical condition. Endogenous diuretics add solids to the urine that are also not detected by ionically-dependent specific gravity tests. Such substances include glucose as a result of diabetes mellitus, and protein molecules from the nephrotic syndrome. Therefore, a urine sample which exhibits elevated specific gravity values on a non-ionic SG test may also not necessarily be indicative of intentional adulteration.

If a non-ionic substance (adulterant) is intentionally added to the urine indirectly through digestion/absorption, such as an osmotic diuretic, it would appear to be invisible on an ionic strength (SG) test. The SG appears normal but in actuality is higher if measured through refractometry, which detects all urinary solids. In this instance, there would be more water in the urine than normal, but the osmotic diuretic would not be found. The urine would therefore be presumed to be unadulterated, since the SG appears normal. Furthermore, the concentration of the illegal substance could be less than the cut-off value as a result of the increased water concentration caused by the diuretic, thereby creating a false negative.

While providing useful information in some instances of the presence of unusual levels of water, ions, creatinine, or solids in a specimen, current adulteration test methods have distinct drawbacks which limit there usefulness in drug testing programs. Current test methods often fail to reveal the intentional use of a diuretic to defeat a drug test. Furthermore, such test methods fail to distinguish artificially inflated specific gravity values resulting from medical conditions as opposed to osmotic diuretics. Thus, it is seen that a need remains for better methods of determining whether a urine sample has been adulterated by the use of either water pill-type diuretics or osmotic diuretics. Accordingly, it is to the provision of such improved methods that the present invention is primarily directed.

SUMMARY OF THE INVENTION

Briefly described, a method for determining whether a urine specimen has been adulterated by the use of diuretics includes measuring the specific gravity and actual creatinine concentration of the urine sample. Normalized urine creatinine concentration is then calculated as a function of the measured urine creatinine concentration and the measured urine specific gravity, the urine specific gravity being adjusted for the difference between the measured specific gravity and a preestablished reference specific gravity for the substantially diuretic free population. The normalized urine creatinine concentration for the person tested is then compared with a range of expected normalized creatinine values for the diuretic-free population, in order to determine if the sample has been adulterated by a diuretic. Preferably this range is between 100 and 600 mg/dl. In order to determine whether the urine specimen has been adulterated by an osmotic diuretic, the specific gravity of the urine specimen is measured by both a total solids method and an ionic strength method. That specific gravity measurement method which results in the larger specific gravity value is then used in the calculation of normalized urine creatinine concentration. If the normalized urine creatinine value is below the expected range then the urine can be deemed to be adulterated by an osmotic diuretic.

A method for determining whether a urine specimen has been adulterated by diuresis includes measuring the specific gravity and actual creatinine concentration of the urine sample. Normalized urine creatinine concentration is then calculated as a function of the measured urine creatinine concentration and the measured urine specific gravity, the urine specific gravity being adjusted for the difference between the measured specific gravity and a preestablished reference specific gravity for the substantially diuretic free population. The normalized urine creatinine concentration for the person tested is then compared with a range of expected normalized urine creatinine concentration values for the diuretic-free population, and also with the actual measured urine creatinine concentration of the specimen. If the value of the calculated normalized urine creatinine concentration is within the expected range of normalized creatinine concentration values and is larger than the actual measured creatinine concentration, the urine specimen is rejectable as being adulterated by diuresis.

DETAILED DESCRIPTION OF THE INVENTION

Figure 1:
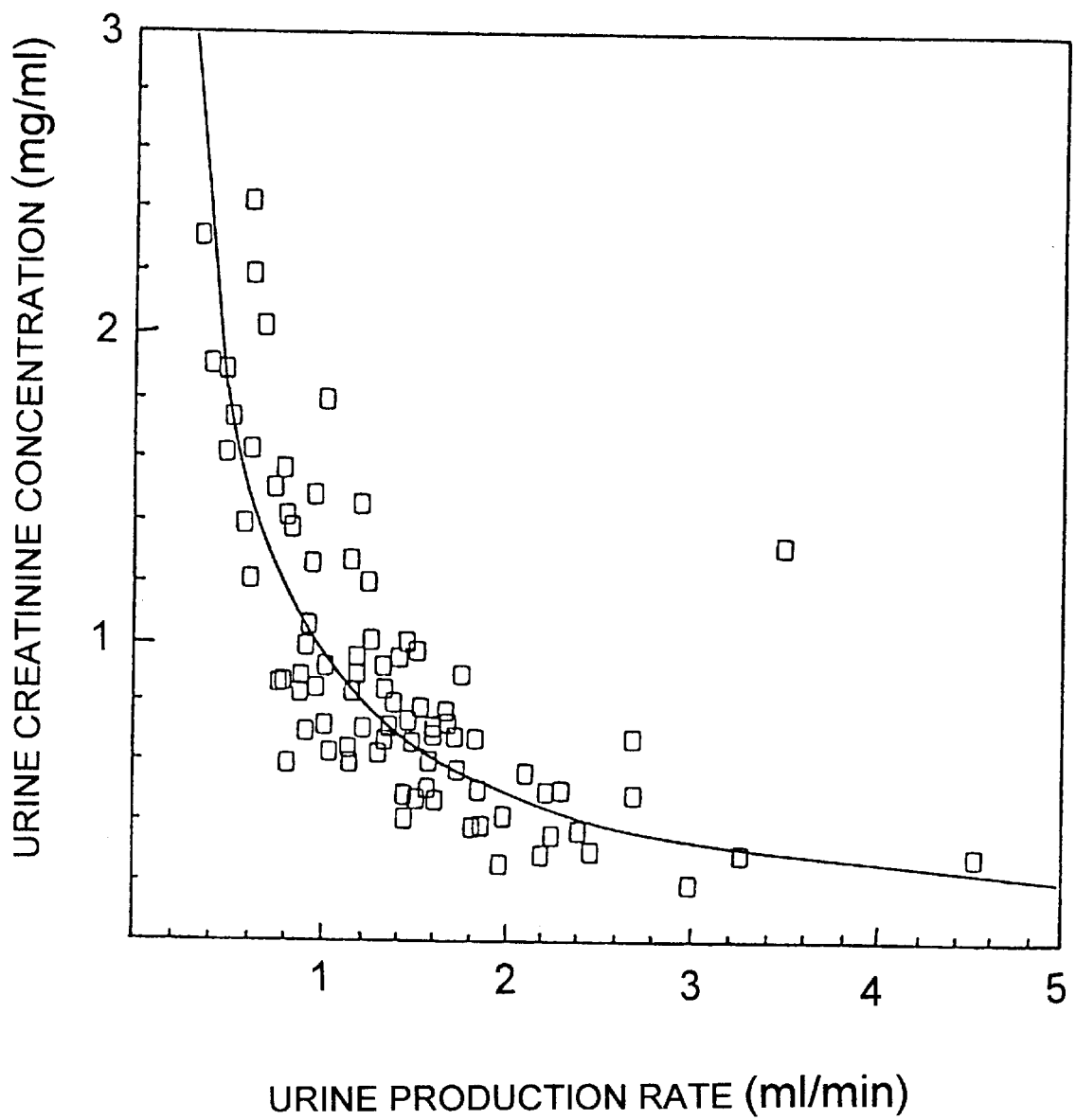
FIG. 1 is a graph of urine creatinine concentration versus urine production rate showing the inverse relationship between urine creatinine and urine production rate, forming a hyperbola using an initial data set.

An individual is first asked to provide a urine specimen in a controlled environment, that is an environment in which a reasonable amount of care is taken to discourage the direct addition of a foreign substance to the person's urine sample or the replacement of the individual's urine sample with that of another individual. Preferably, at this time an initial inquiry is made to determine whether the patient has a medical condition which would ordinarily trigger a flag on an adulteration drug screen. For instance, an inquiry might be made as to whether the individual had recently had any medical procedures conducted involving contrast, radiopaque dyes and whether the individual has a familial history of diabetes. The urine sample is then collected by providing the patient with a standard urine collection bottle into which he or she can urinate. Alternatively, a sample can be collected by catheterization or withdrawn from a urine collection bag. Only several milliliters of urine are required for analysis. Loss of a portion of the sample is not detrimental as long as a sufficient sample remains for analysis.

After the urine sample is collected, it is first tested for the presence of a specific drug or drug metabolite above a predefined concentration cut-off level (as a drug screen). If the concentration of the drug or its metabolites are determined to be present above this level, the individual has tested positive and found to have failed the drug test. If the individual initially passes the drug screen (testing negative), then several properties of the urine are measured, including the amount of solids in the urine (SG), creatinine concentration, urine pH and urine temperature (the latter two if the test is conducted at the collection site) towards determining if the urine sample has been adulterated. It should be noted that urinary solids may be measured by many gravimetric methods, including by weight per cc, hydrometric methods, or refractometry methods (total weight). The refractometry results generally agree with other methods which measure total solids. Furthermore, measurements may be made by osmolality methods (number of particles), or mass related measurements. Measurement of solids may also be by ionic strength/conductivity methods, since urine is for the most part ionic solids. Measurement of ionic strength measures the ions in a sample or the conductivity of the ions in the sample. Such a measurement would fail to include solids having no conductivity such as from the osmotic diuretic isosorbide. However, if adulterants such as osmotic diuretics were added to the urine, the density of the urine would be artificially elevated above a normally expected range and this would be detected in analysis by a total solids method such as refractometry.

Specific Gravity is Measured

The kidneys regulate urine production rates so as to maintain normal blood pressure and blood osmolality. This function of the kidneys is indicated by the urine specific gravity, a physical variable relating to urinary solids and urine volume production rate. Therefore, providing that the individual has initially passed the drug screen, the specific gravity of the urine sample is measured. It should be understood that any of the above described measurements of urinary solids may be used. The specific gravity is measured for the urine at room temperature. Such typically ranges from 1.004 to 1.035. Since the value for specific gravity varies according to temperature, care should be taken to maintain constant measurement conditions at the test site. A digital urinometer by Biovation may be used for this test. The resulting specific gravity value is then compared with an expected range of specific gravity values for a normal test population. If the measured value of the specific gravity falls outside the expected range, and the testing facility has determined that there are no preexisting conditions which would justify the abnormal test results, the test laboratory staff should initially suspect that the urine has been adulterated. For instance, if the urine specific gravity is below the range, then it is possible that overhydration has occurred or water was added to the urine sample. Adulteration by ingestion of diuretics could account for elevated specific gravity values as certain osmotic diuretics such as isosorbide deposit excessive solids in the urine and water pills deposit excessive electrolytes/ions in the urine.

An osmotic or aquaretic diuretic adds solids into the urine thereby drawing more water into the urine, and consequently lowering the concentration of illegal drugs. In such a circumstance, specific gravity is usually too high and there is more solids than expected in the urine. Essentially, with the increase of urinary solids, one sees an increase in water drawn to the urine. At a steady state condition, introducing solids into the urine will result in the kidney drawing water into the urine to compensate. However, it follows that under normal conditions, a higher urine production rate from overhydration will result in a lower urine specific gravity value.

Creatinine Level is Determined

The level of creatinine in the urine is also measured. Creatinine, an end product of glycine and arginine metabolism excreted through the kidneys, is normally measured to evaluate renal function. The creatinine level in human urine usually ranges from 20 to 500 mg. per dl, the range being affected by variables such as age, sex, diet, lifestyle and geographic location. Creatinine levels generally are homeostatically maintained by the body at a constant value for each individual patient over his or her lifetime. Creatinine levels may be determined on many different analyzers, including the TDx REA creatinine system.

After a measured creatinine value has been obtained for the urine sample, it is either compared with pre-established data for the individual or the expected range for a normal test population as a whole. For example, the generally accepted cut-off level for a "diluted" (and therefore adulterated) sample is a creatinine level less than 20 to 30 mg/dl with a SG less than 1.003. If the measured creatinine value falls outside the normally expected range then the test laboratory staff should initially suspect that the urine has been adulterated. Adulteration by ingestion of diuretics could account for an unusual creatinine level as certain osmotic or aquaretic diuretics add excessive solids in the urine thereby drawing more water and creating a low creatinine level. Furthermore, the individual may have over-hydrated himself (diuresis), thereby lowering his creatinine level and specific gravity below the normal range. Finally, the individual may have physically added extra water to the urine sample after it had been collected, thereby lowering the creatinine concentration and specific gravity below the normal range.

After the urine creatinine concentration has been measured this value can be initially compared to the measured specific gravity value to determine if there is a mismatch. For instance, if the measured specific gravity value is high normal and the measured creatinine value is low normal, a laboratory technician should suspect that the urine sample has been adulterated by a diuretic from this mismatch of values. It should generally be understood that specific gravity or creatinine levels may be measured in either order.

Determining Adulteration by Comparing Normalized Creatinine Values with a Range of Expected Normalized Creatinine Values Parameters of a patient's urine, such as pH and specific gravity, vary from one day to the next depending upon the type and quantities of foods and beverages ingested. Additionally, individuals metabolize endogenous substances, at different rates. Due to variations in these daily urine parameters, concentration levels for creatinine, can also vary somewhat over time. Significant tubular resorption does not occur and renal clearance of creatinine is primarily the result of glomerular filtration. The major variable responsible for observed variations in urine creatinine concentrations is tubular resorption or excretion of free water. As between urine production rate and urine specific gravity, a mathematical relationship has also been discovered to exist between creatinine concentrations and urine production rate. As in the relationship between urine production rate and specific gravity, there is an inverse relationship between urine production rate and urine creatinine concentration, i.e. the greater the urine production rate, the less the urine creatinine concentration as illustrated by the initial data set of FIG. 1.

It is now realized that renal excretion rates (mg/dl) for creatinine is relatively constant for any patient during a typical day. This constancy has now been experimentally verified by examining the renal excretion rates of creatinine as a function of urine volume production rate. For example, sequential, complete and timed (1–8 hours holding periods) aliquots of urine for 12 compliant control subjects were collected over 24 to 72 hour periods. For each urine aliquot, urine volume production rate (ml/min), specific gravity and creatinine concentration (mg/dl) were determined. Using this data, a dimensionless, linear relationship was found to exist, that is the same for all patients, between a urine volume production rate factor (UVPRF or normalized urine production rate) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a preselected reference specific gravity usually near 1.030 (i.e. that specific gravity of a normal urine sample at room temperature, typical of a morning void ), v', $$UVPRF=v/v'. \qquad (1)$$

Similarly, in this example, RUCEF factor is defined by the ratio of the creatinine concentration of the most concentrated urine aliquot with a specific gravity usually near 1.030, u', to the creatinine concentration for each urine aliquot collected, u, $$RUCEF=u'/u. \qquad (2)$$

The best fit linear regression line is given by the expression, $$RUCEF=0.942 \cdot UVPRF+0.121 \qquad (3)$$

$$u'/u=0.942 \cdot v/v'+0.121 \qquad (4)$$

where statistical evaluation results in an adjusted squared multiple R=0.985, a standard error of the estimate=0.242, and a F-ratio=4965.

Therefore, contrary to the traditional teachings of those skilled in the art, urine drug and metabolite concentrations, as well as endogenous substance concentrations, u, are inversely related to the volume of urine produced by the kidneys, v, clearly demonstrating that the product (u·v) is constant at any particular time point and urine pH.

Since (u·v) at any time is a constant, steady-state value, it follows that from Equation (4) some empirical mathematical relationship must exist between u and v such that given an arbitrary urine volume production rate v' and an equivalent u' at a reference point (a specific gravity of 1.030):

$$\{u \cdot v\}_{sg\ actual} = \{u' \cdot v'\}_{sg\ 1.030} \qquad (5)$$

or upon rearrangement for u' gives, $$u'=u \cdot (v/v') \qquad (6)$$

where the products given in Equation (6) are those measured for a spot urine sample collected with an actual specific gravity and a corrected specific gravity typical of a morning void of 1.030.

Following a first collection of data as reflected in FIG. 1, independent data was gathered from 96 patients being followed in a renal disease clinic. Data available from these patients included 24 hour urine volumes, urine specific gravity, urine creatinine concentration, serum creatinine concentration, creatinine clearances measured from 24 hour collections, presence of protein and glucose in urine, urine osmolality, patient sex, age, lean body weight, total body weight, height and diagnosis.

Using these controlled urine collections, a urine volume production rate v' of 0.58 ml/min for persons with reasonably normal renal functions at a specific gravity of 1.030 was measured. A specific gravity factor was then calculated using the ratio (rsg−1.000)/(msg−1.000), where rsg is a preselected test reference specific gravity, which in this case is equal to 1.030, and where msg is the measured specific gravity. The specific gravity factor is an adjustment of the measured specific gravity value to account for the difference between the measured specific gravity value and a preselected test reference specific gravity value for the substantially diuretic-free population. The specific gravity factor essentially normalizes the measured creatinine value to account for variations in measured specific gravity values.

Figure 2:
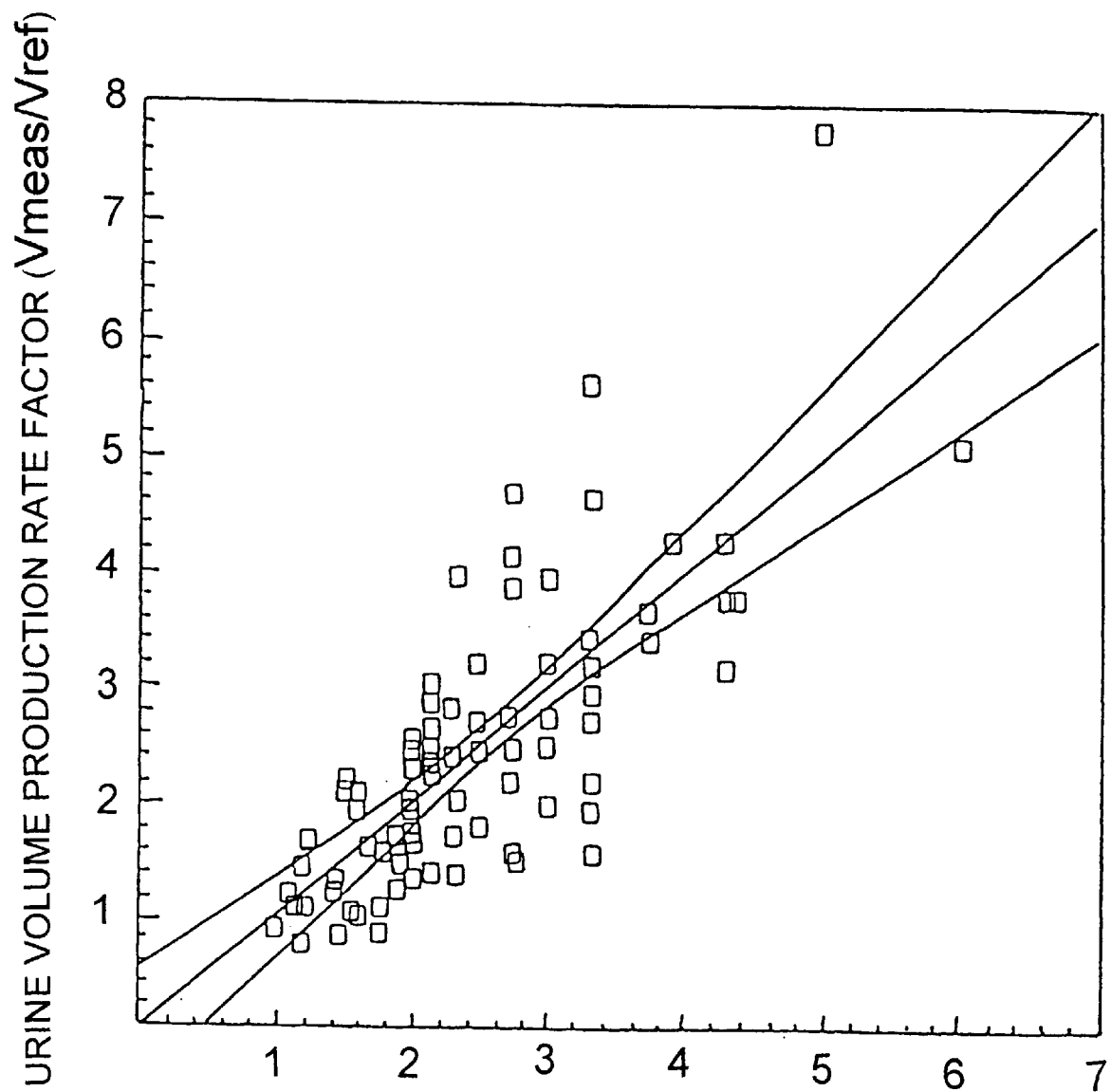
FIG. 2 is a graph of urine volume production rate factor versus urine specific gravity factor, showing a slope of one and a zero intercept and demonstrating their substantially linear relationship.

It has been found that a linear relationship exists between the urine volume production rate factor (normalized urine production rate) and the specific gravity factor, (SGF) as shown in FIG. 2 giving a slope of 1 and a zero intercept and given as follows:

$$UVPRF=v/v'=SGF \qquad (7)$$

Calculating Normalized Urine Creatinine Concentration (nu, NCR, or NCRE as expressed in the accompanying figures)

Substituting Equation (7) into Equation (6) the specific gravity normalized creatinine concentration, nu (or NCRE, since we are measuring creatinine) is then calculated by adjusting the actual urine creatinine concentration, u, for compounding effects of urine specific gravity at 1.030:

$$nu=u'=u \cdot (v/v')=u \cdot UVPRF=u \cdot SGF \qquad (8)$$

The NCRE is therefore the creatinine concentration, taking into account variables such as the compounding effects of urine specific gravity, patient body weight, lean body mass, person's sex, and age. In this instance, however, only specific gravity is considered.

Using Osmolality Measurement in Lieu of Specific Gravity Measurement in Calculations It has been noted that specific mathematical relationships exist between the rate of urine formation (ml/min) and the concentration of creatinine in the urine. A relationship also exists between these variables and urine specific gravity. Generally, the relationships between SGF and v/v' apply to persons with normal renal function. However several situations exist in which the SGF, especially when measured by refractometry or a hydrometer, is not directly related to v/v', thus creating inaccuracies in the relationships heretofore described. Such a situation occurs whenever the urine contains a significant amount of protein and/or glucose. Occasionally this can also occur whenever urinary cleared, radiopaque dyes are used for diagnostic purposes. Each of these compounds can affect the refractive index or drag coefficients for a spinning hydrometer. In situations such as these, the presence of the abnormal components results in the specific gravity value being artificially elevated. For example, protein in the urine, which is mainly albumin, causes the specific gravity to increase by about 0.003 units for every 1000 mg of protein/100 ml urine. The presence of glucose results in an increase of about 0.004 units for every 1000 mg of glucose/100 ml urine. If the presence of these influencing compounds is not considered, the specific gravity utilized in the correlation is inaccurate. This inaccuracy is readily apparent because the v/v' from the calculated SGF will fall outside of the expected range, alerting the clinician to a possible unusual situation. It will appear that the urine specific gravity is too high for the amount of urine produced. In this scenario, additional urine tests can be done to quantify the amounts of protein, glucose and radiopaque dyes. Once these figures are obtained, corrections can be applied to the calculations. For example, another urine sample can be collected after the radiopaque dye is out of the urine and numerical corrections to the refractometer or hydrometer specific gravity values can be made for protein and/or glucose. The corrected specific gravity is determined by subtraction so as to remove the effect of the abnormal urine components. Once these corrections are made, the normally expected relationships between SGF and v/v' may be noted.

However, in lieu of using SGF as a measure of urine concentrating ability, specific gravity being the mass of a unit volume of solution/mass of a unit volume of pure solvent, urine osmolality factor (hereinafter UOF) can also be used. Osmolality is the number of osmotic particles per unit volume of pure solvent and is not sensitive to temperature variations as is specific gravity. A common relationship exists in scientific literature relating urine osmolality to urine specific gravity. For instance, urine osmolality, measured in mOSM, is equal to 37500(SG-1.000). The urine osmolality factor is defined as the ratio of the urine osmolality at a specific gravity of a reference point, such as 1.030, to the urine osmolality equivalent at the actual urine specific gravity. Using this equation, the following figures may be generated for protein/glucose free urines.

EXAMPLES

|  | Measured Specific Gravity | Calculated Specific Gravity Factor | Measured Osmolality | Calculated Urine Osmolality Factor |
|---|---|---|---|---|
| sample 1 | SG 1.003 | SGF 10 | Osm 112.5 | UOF 10 |
| sample 2 | SG 1.015 | SGF 2 | Osm 562 | UOF 2 |
| sample 3 | SG 1.030 | SGF 1 | Osm 1125 | UOF 1 |

It is therefore evident from this data that SGF and UOF values are equivalent and either one may be used in the application of this invention.

Figure 3:
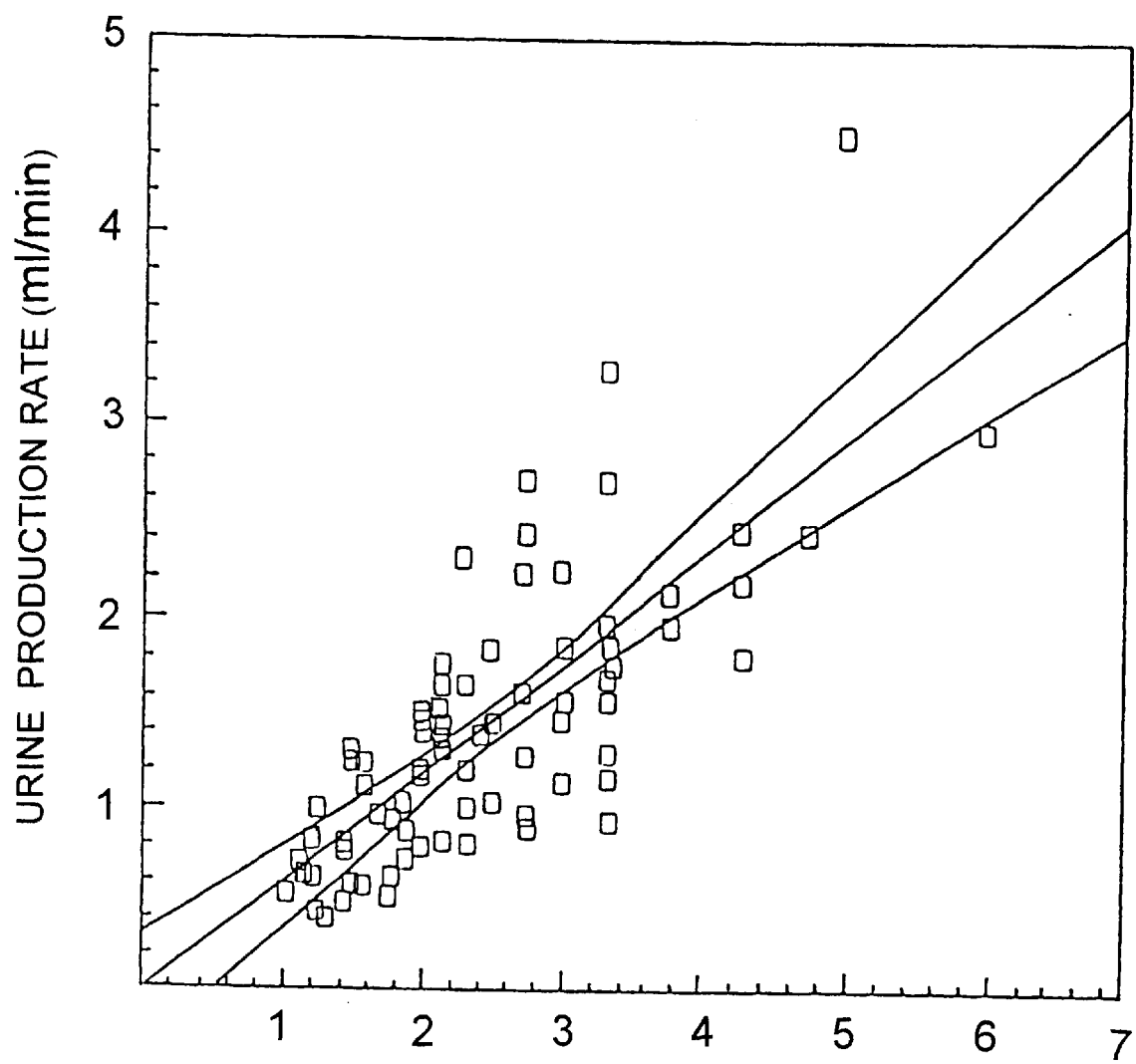
FIG. 3 is a graph of urine production rate versus urine specific gravity factor (SGF) using independent data and showing their substantially linear relationship.
Figure 4:
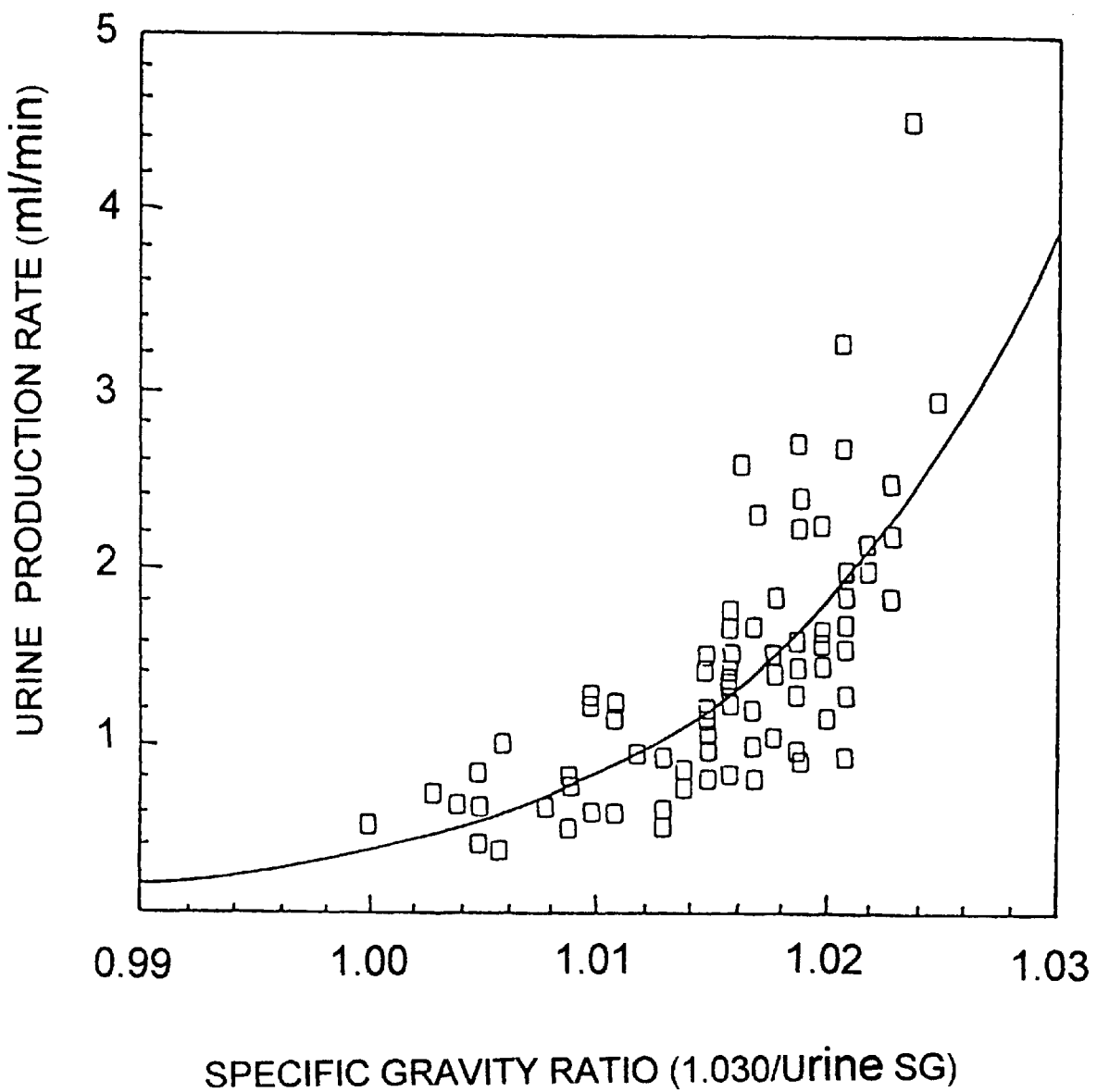
FIG. 4 is a graph of urine production rate versus specific gravity ratio (1.030/urine SG).

The independent data was also plotted by urine production rate (ml/min) versus various mathematical formulations of urine specific gravity as illustrated in FIGS. 3 and 4. Although several methods exist for plotting specific gravity or its equivalent, osmolality, on the x-axis, i.e., SG ratio= 1.030/SG, SGF or even SG, the SGF and UOF relationship are preferable.

Figure 5:
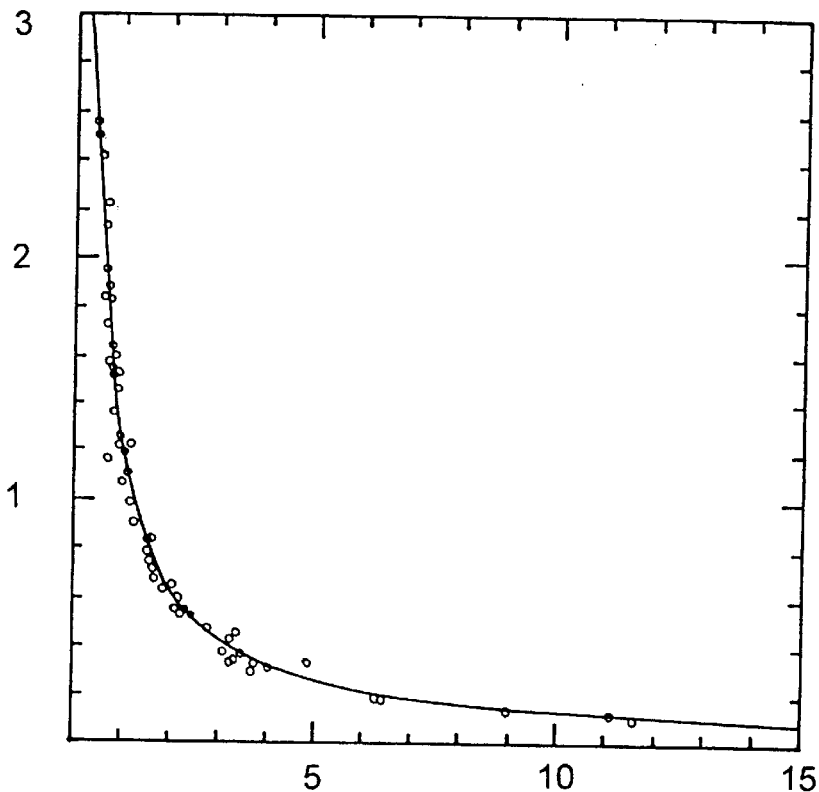
FIG. 5 is a graph of urine creatinine concentration versus urine production rate showing the inverse relationship between urine creatinine and urine production rate, forming a hyperbola using independent data.

As a further example for demonstrating in greater detail the inverse relationship between urine creatinine and urine volume production rate, urine creatinine concentration was again plotted against urine production rate revealing the hyperbola of FIG. 5.

The human kidney dilutes the urine at the end stage of processing and filtration. If it requires water for urine production, concentration of substances in the urine goes down, whereas if it does not require water for urine production, concentration of substances in the urine remains high. FIGS. 1 and 5 demonstrate how the concentration of a substance which is normally produced by the body i.e. creatinine, has an inverse relationship to urine production rate, so that as urine production rate increases, the concentration of urine creatinine decreases for normal functioning kidneys, and where there are no extraneous substances which should not be present in the urine. If a person were to drink large quantities of liquid to produce a large quantity of urine, one would expect to see a low urine creatinine concentration.

Figure 6:
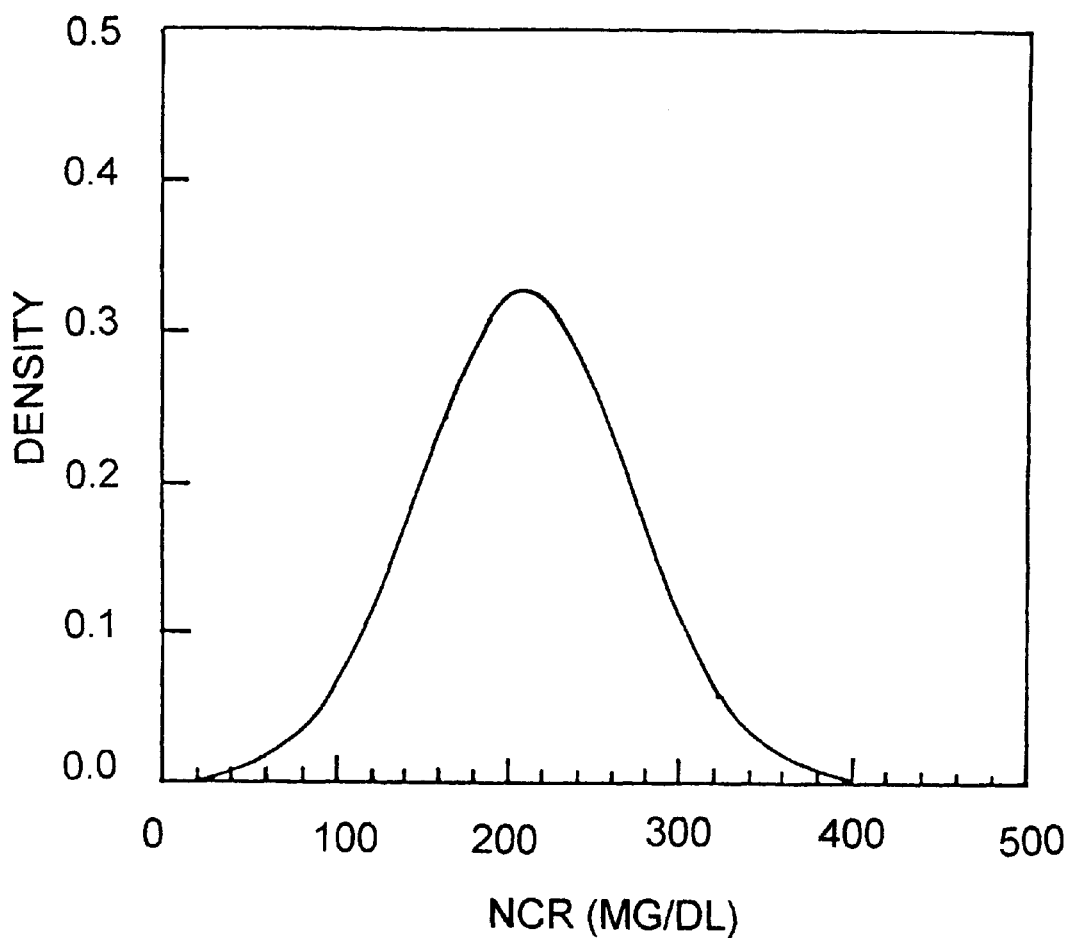
FIG. 6 is a graph of density versus normalized creatinine values.

Comparison of Normalized Creatinine Values With Established Normalized Creatinine Values The normalized urine creatinine concentration is then compared to either established historical values for the patient or expected ranges for normalized creatinine concentrations from normal diuretic free independent patient databases, as illustrated in FIG. 6. FIG. 6 plots normalized creatinine values (normalized by SG ionic strength) against density values (counts for samples). The curve demonstrates that for the tested population, the NCRE should fall between a certain range for a normal unadulterated test sample. The lower the measure of specific gravity, the higher the NCRE, and vice versa. If the calculated normalized urine creatinine is significantly out of the range of expected values then the urine is deemed to be adulterated. Even if an individual does overhydrate in an attempt to affect his/her drug test, by using a specific gravity factor in the normalization equation, one can calculate the correct amount of creatinine in the urine without the added water. The creatinine normalization equation does adjust for over hydration. If there is too little or too much creatinine, one would realize that the urine had been adulterated.

Figure 7:
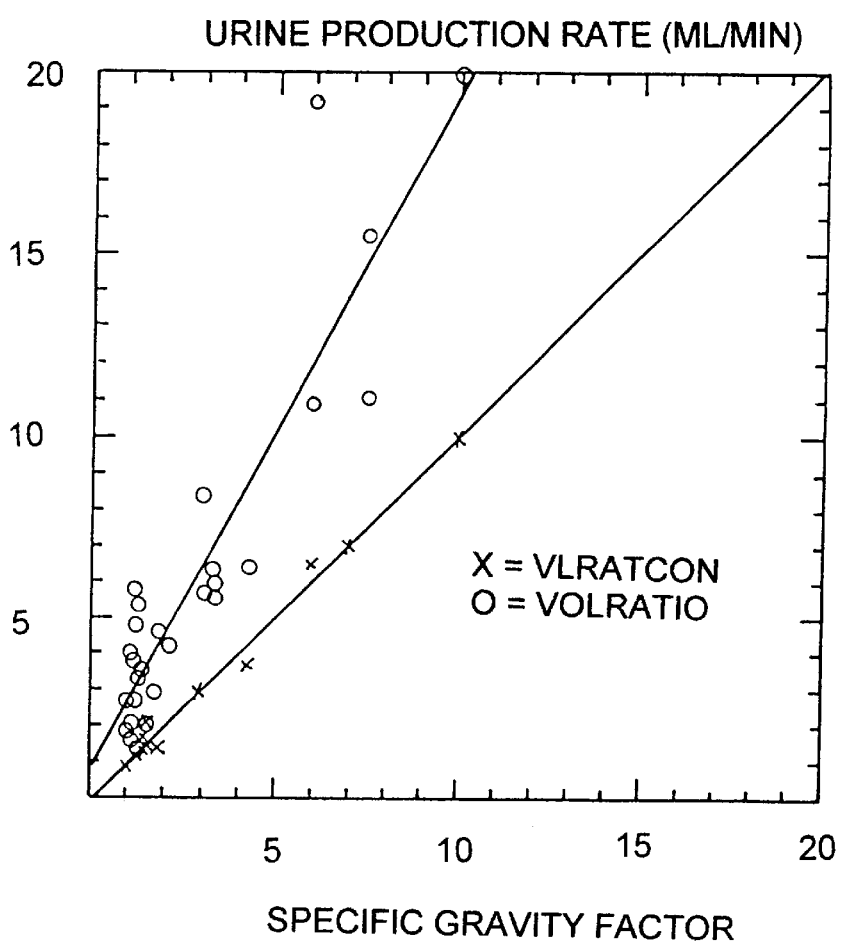
FIG. 7 is a graph of normalized urine production rate versus specific gravity factor.

FIG. 7 illustrates the relationship between normalized urine production rate (normalized urine production rate being the volume ratio as described earlier by the ratio v/v') as compared with specific gravity factor. If an individual were to take an osmotic diuretic in order to pass a drug test, such a diuretic could place ionically invisible solids in the urine which draw excess water. In this circumstance the concentration of the creatinine in the urine test sample would be too low for the specific gravity of the urine (the specific gravity would be unusually high as determined by using refractometry, despite a normal reading on an ionic strength test). Essentially, in this scenario there would be too much water for the dissolved solids present and as a result, the creatinine level would be too low. In this situation, the calculated NCRE would be too small. For example, while the SGF is supposed to be 10, it is in fact 1. The calculated value of NCRE is also too low. For the same SGF there is too much water present i.e., for the same amount of solids, there is too much water. This situation is illustrated in FIG. 7, with the lower line illustrating the expected values and the upper line representing results from use of an osmotic/aquaretic diuretic and subsequently higher urine levels.

A "water pill" diuretic, such as Lasix (for lasts six hours) puts ionic solids in the urine. This diuretic increases the loss of both electrolytes and water from the body. Consequently, this type of diuretic causes the excretion of more solids from the body than are physiologic by inhibiting sodium transport or chloride transport. The use of these diuretics puts unexplained solids in the urine. These solids may be measured ionically, and always make the specific gravity higher than expected.

The water pills work in the following manner. If the body excretes chloride ions, as a result of ingesting these types of diuretics, water becomes associated with the chloride, which is normally expected for chloride ions. However, excess water is not normally present for the amount of creatinine present in the specimen. The specific gravity is also too high for the amount of water present. If the specific gravity correction factor SGF is then used i.e., for creatinine, the NCRE always appears too low.

For these types of diuretics, if one were to measure for creatinine, the value would always be too low for the specific gravity measured by ionic strength. A comparison of these two measurements would therefore definitively reveal adulteration and subsequently require retesting.

However, if an individual were to take an osmotic diuretic such as isosorbide, which is not an ion, the solids from the diuretic would not show up as ions. Therefore, the specific gravity measured would allegedly be the correct one for the amount of creatinine present in the urine sample, since the specific gravity measured by the ionic strength does not take into account non-ionic solids. In this instance, only a specific gravity measured by a total solids method would take into account these additional solids.

Comparison of Normalized Creatinine Values with Actual Measured Creatinine Value The calculated normalized creatinine value may also be compared with the actual measured creatinine value. If the calculated NCRE is a larger value than the actual measured creatinine level, and the NCRE is within the normal expected range, it is likely that the specimen has been adulterated by diuresis.

Figure 8:
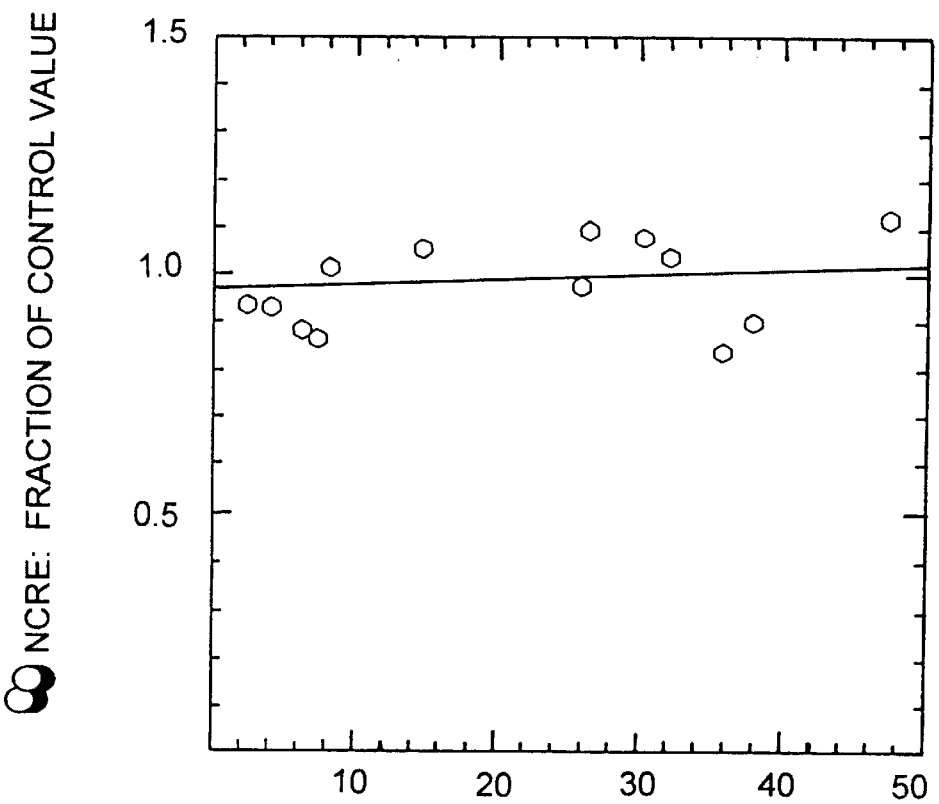
FIG. 8 is a graph of normalized creatinine as a fraction of the control value versus sampling time in a controlled case by hours.

The following examples are illustrative of the analysis to be performed utilizing the test method for diuretic adulteration. In this regard, FIG. 8 illustrates for a control value, how normalized creatinine concentration levels should be plotted for a typical test subject over a period of time.

Example 1

Figure 9:
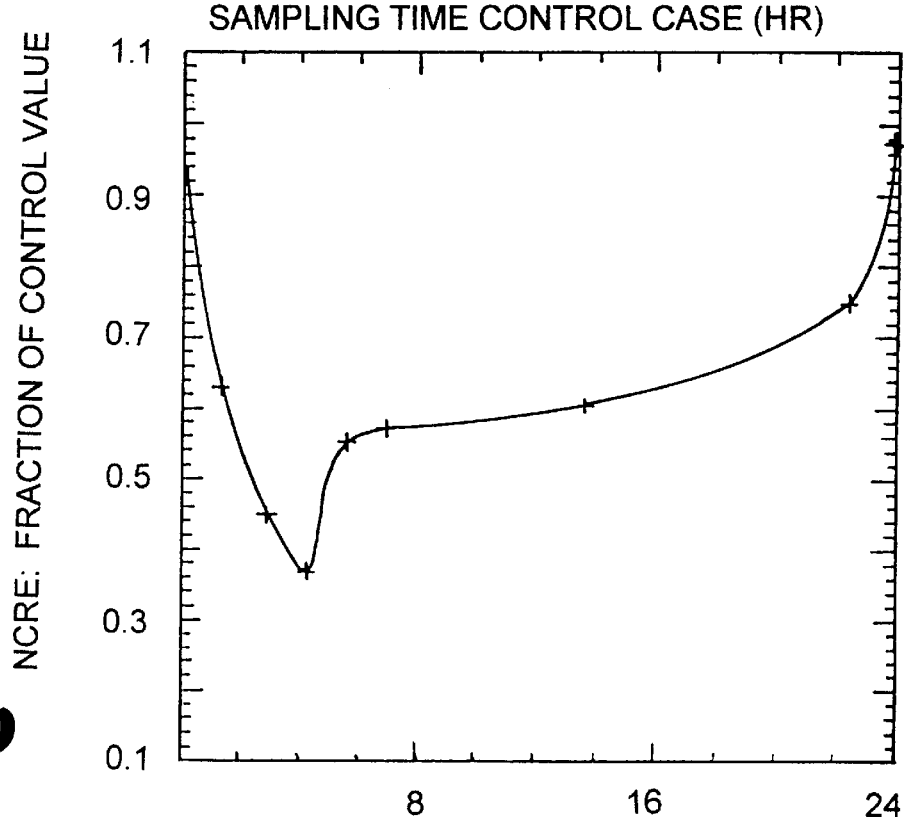
FIG. 9 is a graph of normalized creatinine as a fraction of control value versus sampling time after ingestion of hydrochlorothiazide by the hour.

FIG. 9 illustrates the effect on the control value of the ingestion of the diuretic hydrochlorothiazide. In this situation where there is free water in the urine sample, the NCRE appears to be too low, as compared to the control value of FIG. 8. This would indicate to the testing laboratory that the urine sample had been adulterated by a diuretic, or at the very least, the addition of free water to the test sample.

The specific gravity in this instance is too high for the creatinine present, thereby lowering the specific gravity factor, and consequently the calculated normalized creatinine level. As a result, the graph dips below the control value of FIG. 8. In this example, the tested individual would have passed the test for specific gravity alone and the overall drug test would have been negative. While the adulteration may have been caught on a creatinine level cutoff itself, it was assured detection on the normalized creatinine comparison.

Example 2

Figure 10:
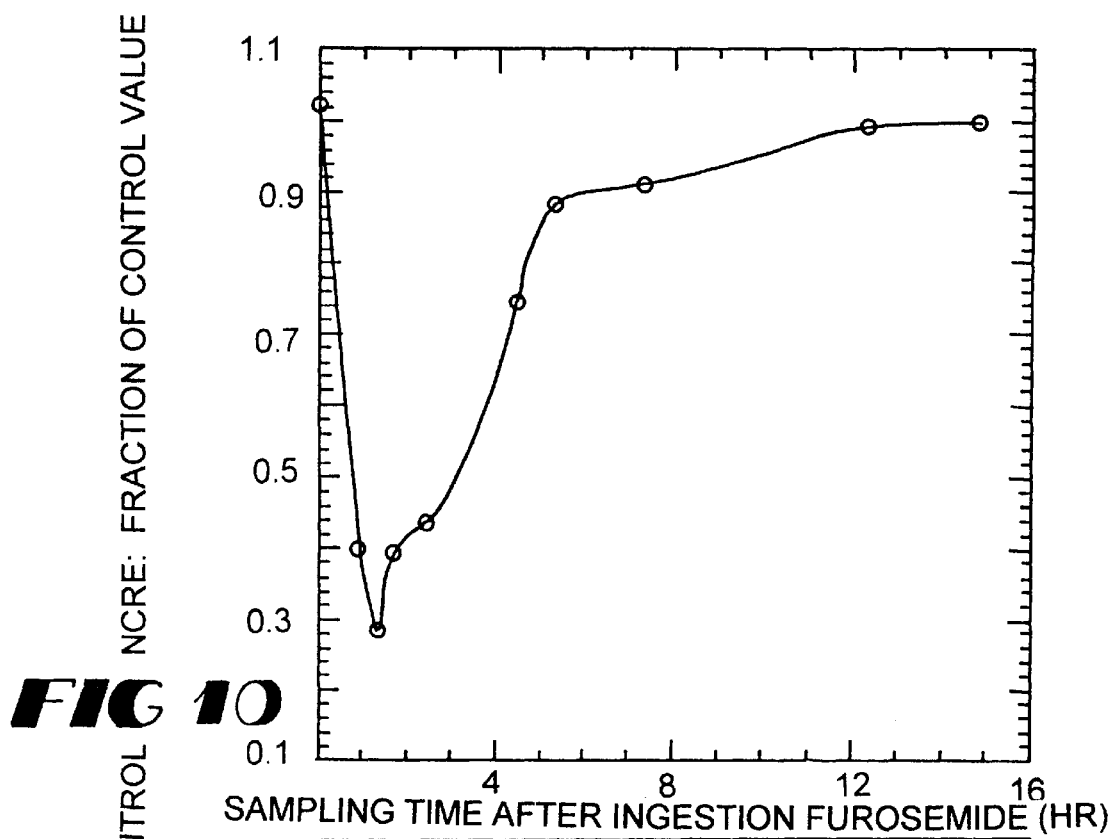
FIG. 10 is a graph of normalized creatinine as a fraction of controlled value versus sampling time after ingestion of furosemide (lasix) by the hour.

FIG. 10 illustrates the effect of the water pill diuretic Lasix on the normalized creatinine level. In this example the normalized creatinine level drops dramatically with respect to the control value of FIG. 8, and stays depressed with respect to the control value for a six hour period.

Example 3

Figure 11:
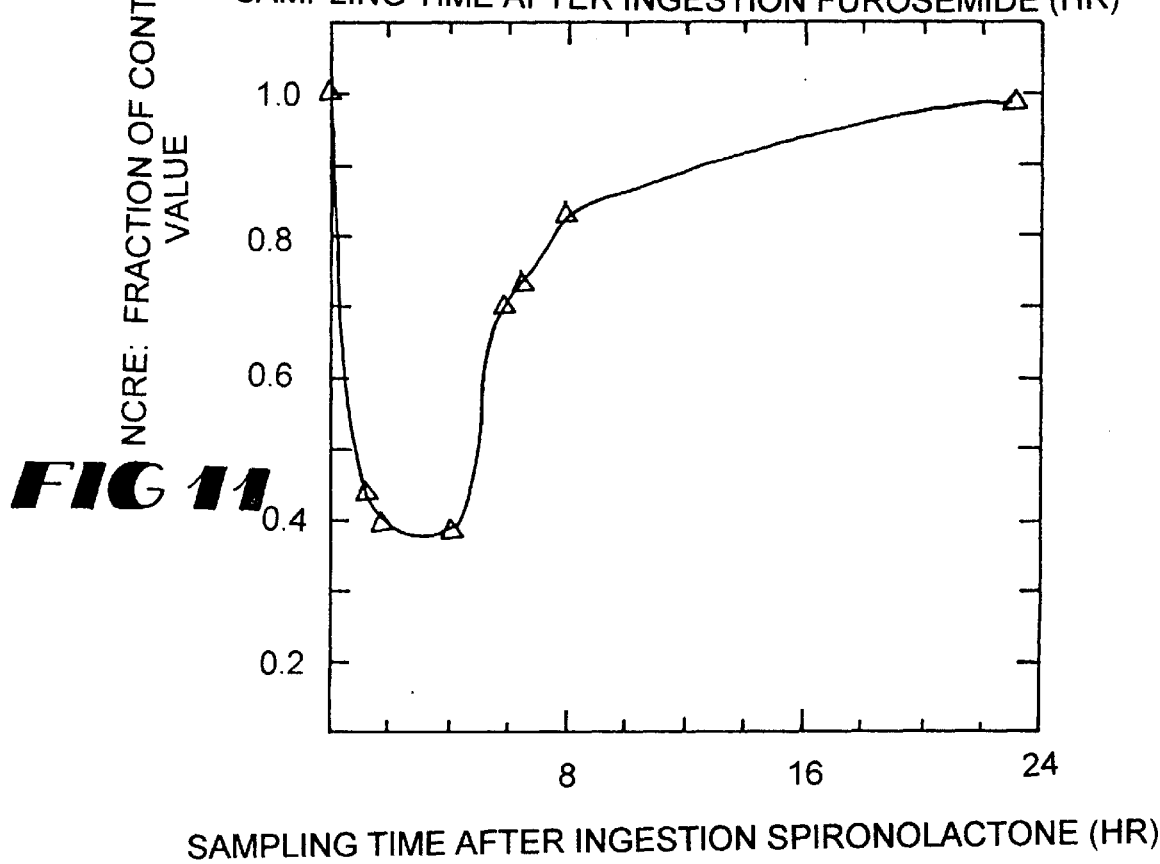
FIG. 11 is a graph of normalized creatinine as a fraction of control value versus sampling time after ingestion of spironolactone by the hour.

A further example in FIG. 11 of the effect of a water pill diuretic, in this case spironolactone, indicates that water pill diuretics consistently lower normalized creatinine levels below their expected control values, as illustrated in FIG. 8. The specific gravity values are too high for the amount of creatinine present in the urine sample. In this example, one dose of the diuretic spironolactone diluted the sample by a factor of 2.5.

Example 4

Figure 12:
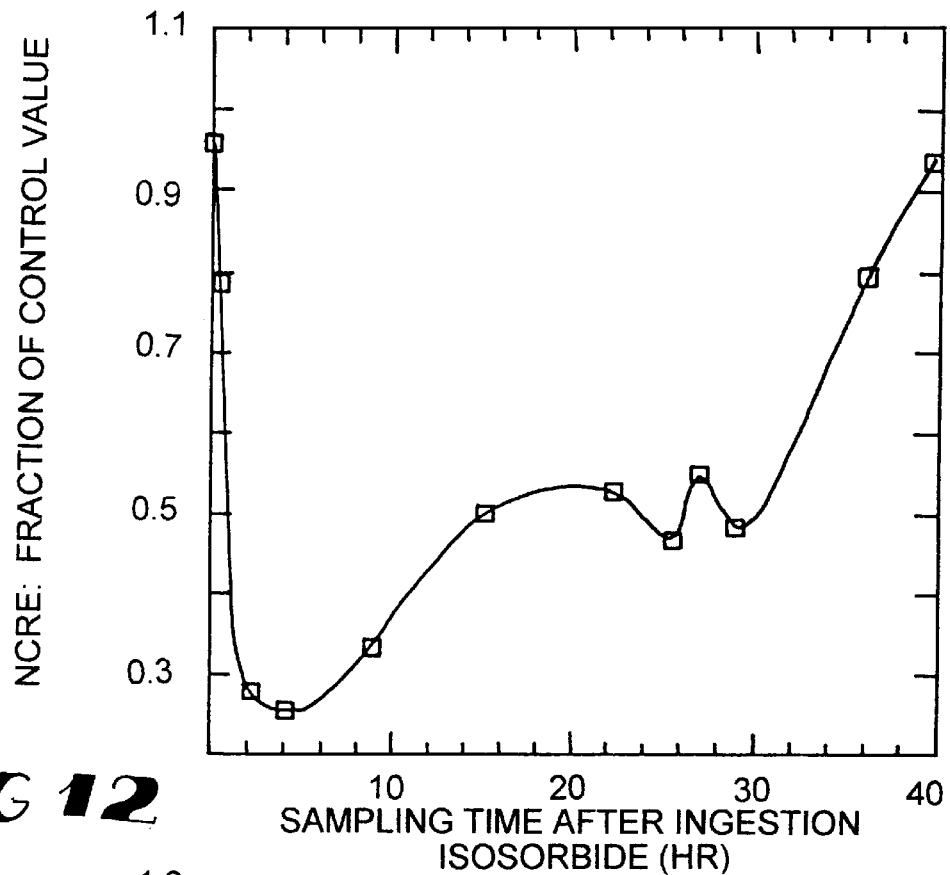
FIG. 12 is a graph of normalized creatinine as a fraction of control value versus sampling time after ingestion of isosorbide by the hour.
Figure 13:
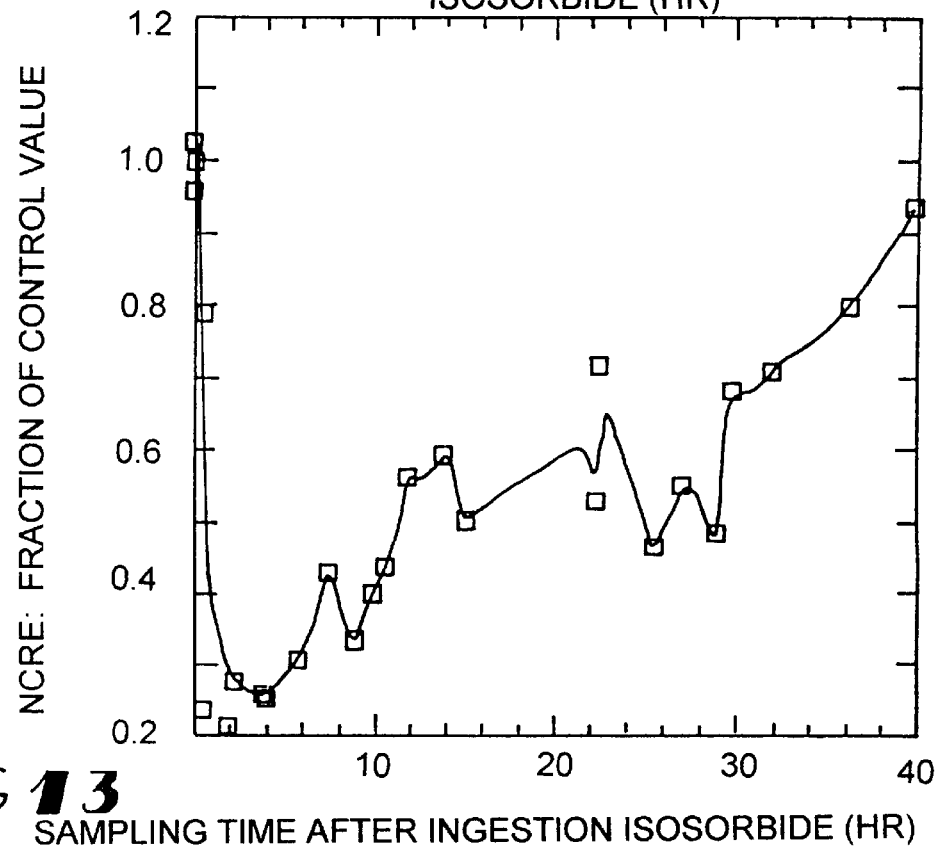
FIG. 13 is a graph of normalized creatinine as a fraction of control value versus sampling time after ingestion of isosorbide by the hour.

FIGS. 12 and 13 illustrate the effect of the osmotic diuretic isosorbide on normalized creatinine levels. The drug presented a long lasting diuretic dose. In this example the specific gravity of solids in the urine is too high for what the body should have eliminated under normal conditions. The high specific gravity value lowers the calculated specific gravity factor, which in turn dramatically lowers the normalized creatinine value with respect to the control values of FIG. 8. In these examples electrolytes drawn into the urine raise the specific gravity values of the samples.

Figure 14:
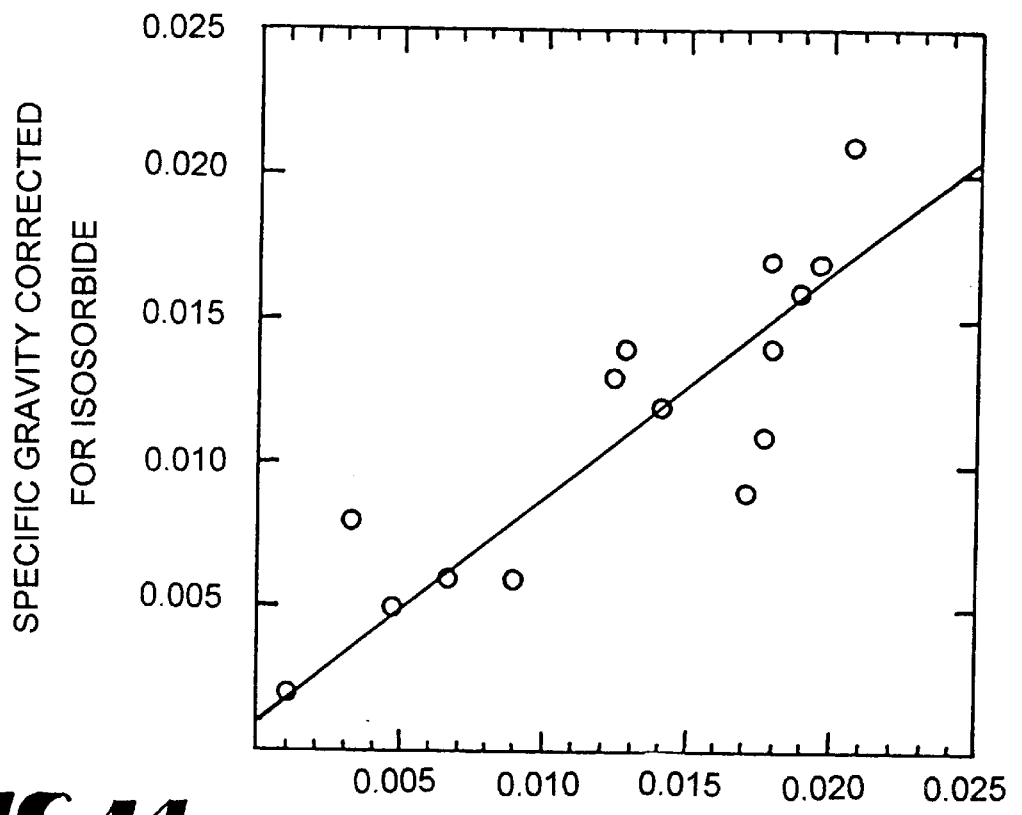
FIG. 14 is a graph of specific gravity corrected for isosorbide versus specific gravity using ionic strength showing a linear relationship.

FIG. 14 illustrates the specific gravity of urine test samples containing isosorbide calculated by the ionic strength method versus the specific gravity corrected to account for the presence of isosorbide.

Figure 15:
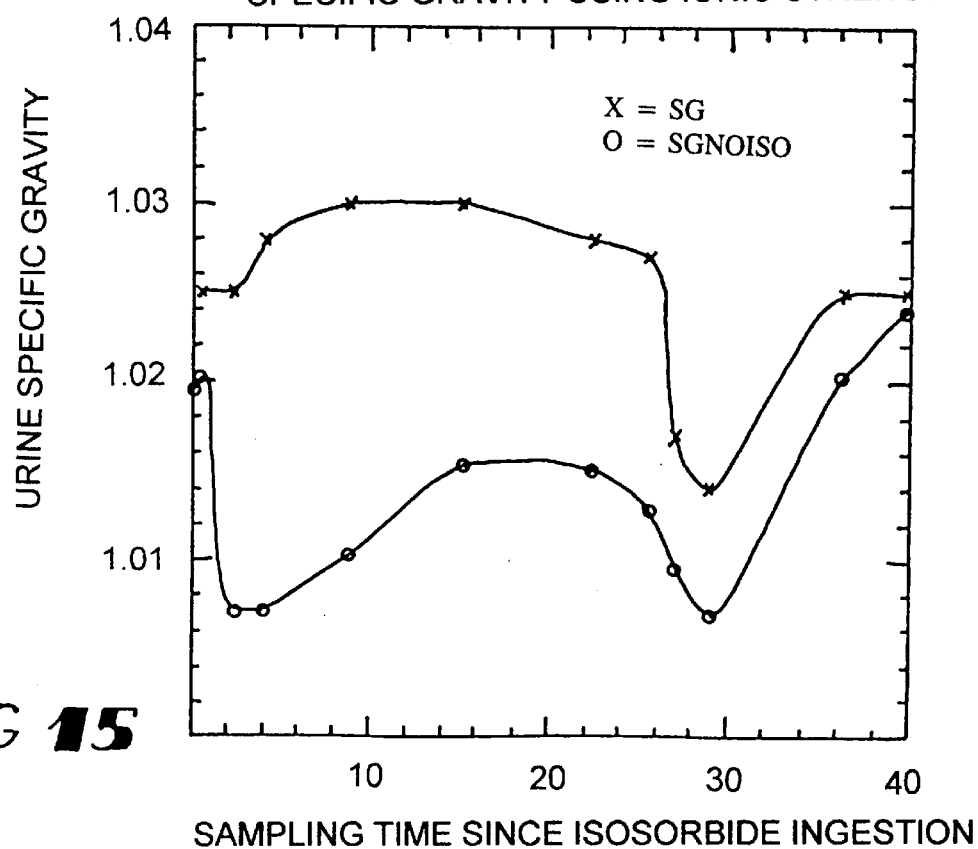
FIG. 15 is a graph of urine specific gravity versus sampling time since isosorbide ingestion by the hour.

FIG. 15 is a double run graph illustrating the variation between a specific gravity measured by ionic strength methods as opposed to refractometer methods and serves as a corollary to FIG. 14. The urine sample tested included isosorbide. Since isosorbide deposits non-ionic solids in the urine, such solids fail to be detected by an ionic strength-based specific gravity test. Hence the lower curve on the graph demonstrates the specific gravity under the ionic strength measurement methods and the upper graph demonstrates specific gravity based on total solids through the refractometry method. The total solid method demonstrates a higher specific gravity since it is accounting for both ions and other solids present in the urine sample. The lower curve reflects the measurement of ions only. Under the ionic strength measurement method the individual may obtain a false negative test result. The effect of these specific gravity differences on the calculated NCRE would be dramatic and could clearly indicate adulteration.

Figure 16:
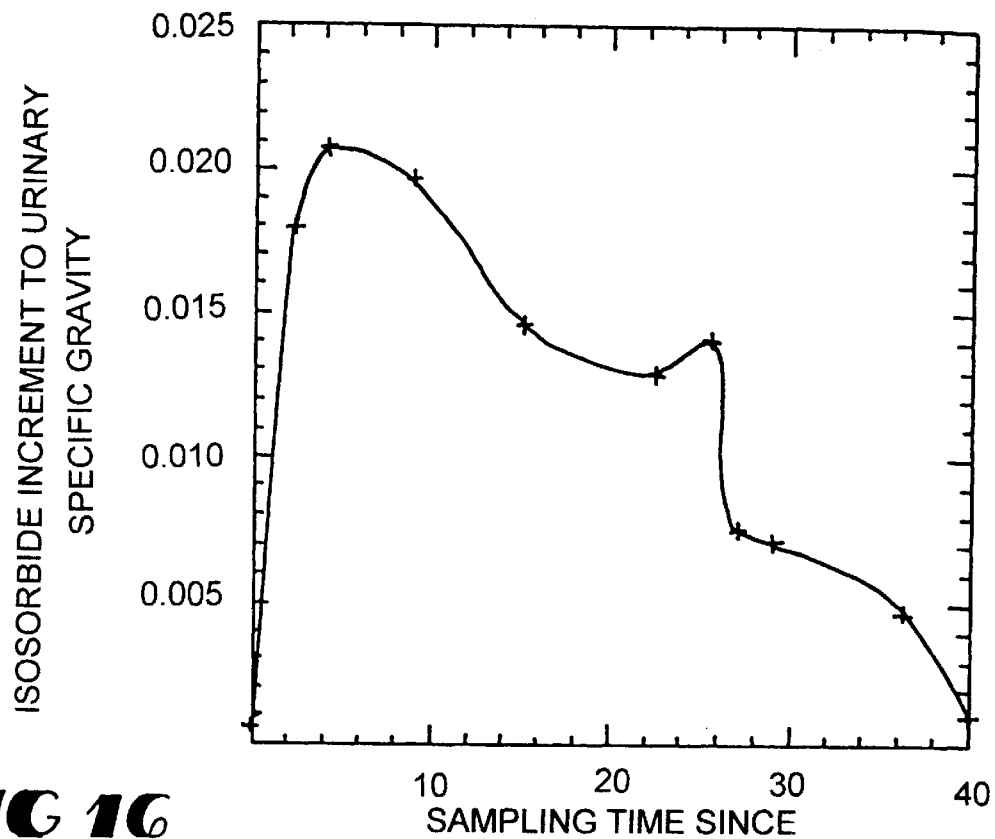
FIG. 16 is a graph of isosorbide increment to urinary specific gravity versus sampling time since isosorbide ingestion by the hour.

FIG. 16 illustrates the difference between the two curves in FIG. 15 and shows the isosorbide incremental affect on urinary specific gravity over a period of time.

Example 5

Figure 17:
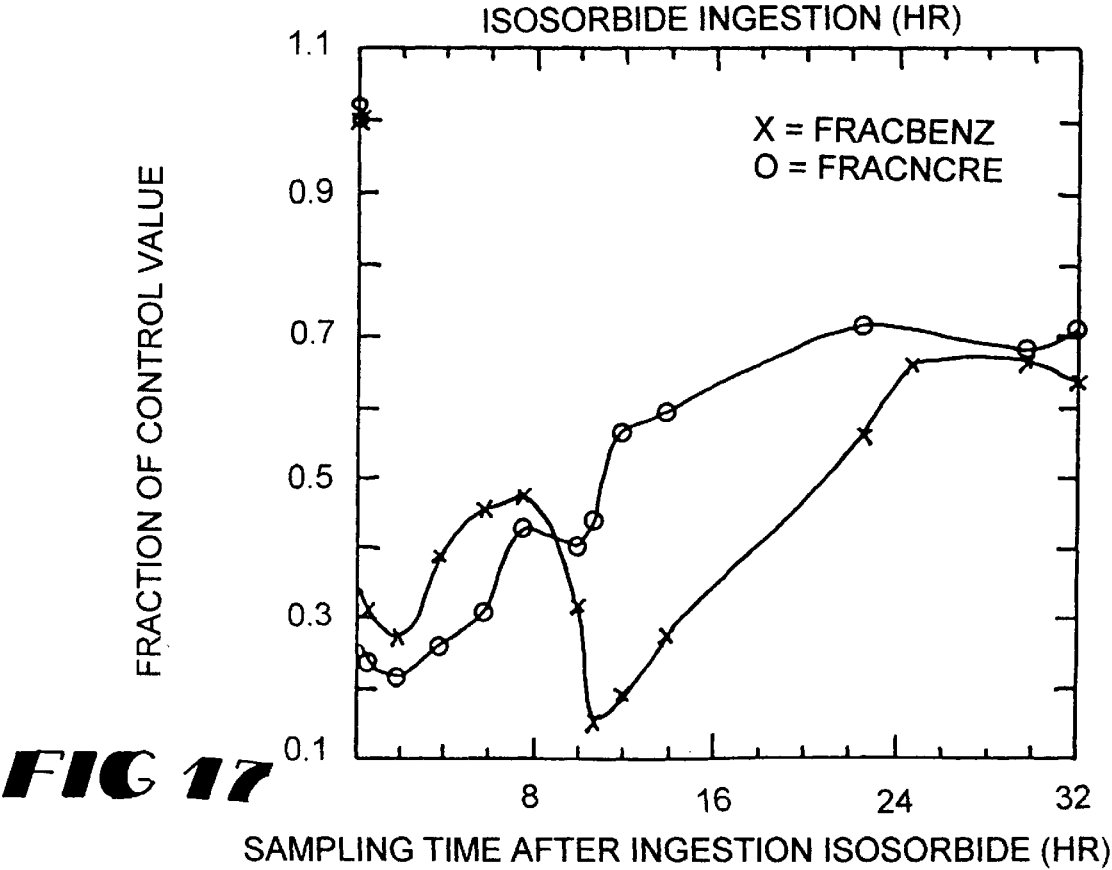
FIG. 17 is a fraction of control value versus sampling time after ingestion of isosorbide by the hour.

FIG. 17 illustrates the effect of isosorbide ingestion on a urine sample containing the drug valium (BENZ for benzodiazepine). The individual taking the drug screen test would obtain a false negative result on the drug test since the concentration of the drug in the urine has been lowered by the diuretic effects of the isosorbide. However, an analysis of the NCRE and specific gravity value reveals that an adulterant diuretic has been ingested which has effectively lowered the NCRE well below the expected value. The testing laboratory would then require a retesting of the individual, hopefully under closer scrutiny.

Figure 18:
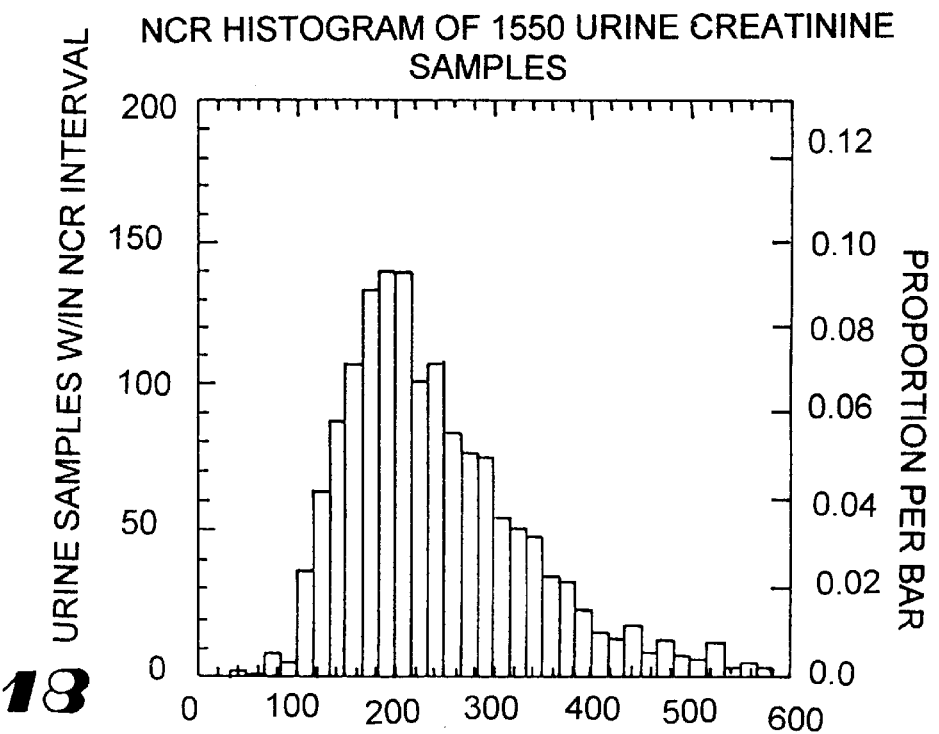
FIG. 18 is an NCR Histogram of 1550 urine creatinine samples showing urine samples with NCR interval versus NCR, specific gravity normalized urine creatinine.
Figure 19:
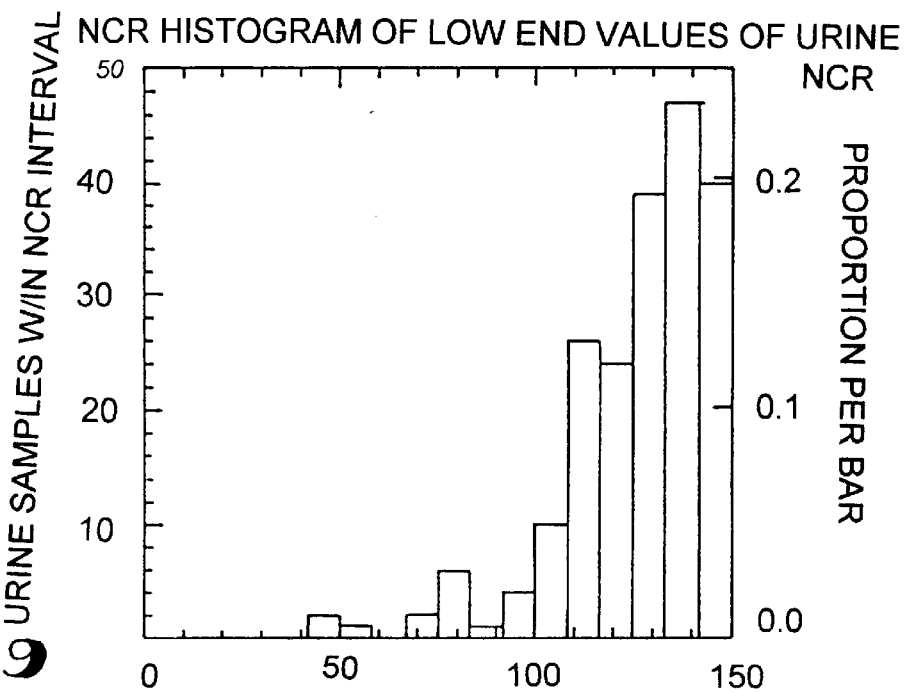
FIG. 19 is an NCR Histogram of low end values of urine NCR showing urine samples with NCR interval versus NCR, specific gravity normalized urine creatinine.

Essentially under this method one calculates normalized urine creatinine to see whether creatinine levels are too low for a normal person, i.e. whether there is too much water for the person in the specimen. Such high water levels are not physiological, and not the result of hydration, as the creatinine level would be flat if the excess water had been the result of hydration, i.e., there would not be a disproportionately high specific gravity value since high urine production rate usually results in a lower specific gravity value. While the normalization equation corrects for hydration, the equation does not correct for the addition of water pill diuretics and osmotic diuretics into the urine. In this regard, total solid methods (such as the refractometer) are the most accurate methods for measuring non-ionic urinary solids as opposed to urinary solids. Use of osmotic diuretics would always produce a higher specific gravity value by a total solids specific gravity method than by an ionic strength specific gravity method. Measurement of these solids in the urine by a total solids specific gravity method, followed by a comparison of the calculated normalized creatinine level would then specifically reveal the use of osmotic diuretics (and generally water pills). In this regard, a laboratory would utilize a histogram such as those found in FIGS. 18 and 19 to determine where the test subject's normalized creatinine level falls with respect to a normal non-diuretic test population. A low value around 100 and an upper value above 600 would be appropriate range limits, as determined by test sample data from 1550 urine creatinine samples. If the normalized urine creatinine value is below the range it is likely that the urine has been adulterated via a diuretic or overhydration. In this regard it should be noted that if the normalized urine creatinine concentration is above the accepted range, it is likely that the tested individual substituted the urine of a non-human animal for its test sample or added secondary creatinine to the specimen.

It thus is seen that test methods are now provided for evaluating whether a urine sample has been adulterated through the use of a diuretic or other means. The method utilizes the measured specific gravity value for the urine sample (through ionic strength and total solids method), the measured creatinine value for the sample, and the calculated normalized creatinine value as an indication of the level of dilution of the urine sample. The normalized creatinine values are then compared to expected ranges for normal urine samples as indications of adulteration. The test methods overcome limitations of existing specific gravity chemical test kits. The test methods are not limited by a chemical reagent which indicates only a narrow specific gravity range. The test methods are not dependent on ion measurement for specific gravity measurement, which are prone to inaccuracy. Finally, the test methods also adjust measured creatinine concentrations to account for artificially inflated specific gravity values resulting from diuretic usage.

While this invention has been described in detail with particular references to the preferred embodiments thereof, it should be understood that many modifications, additions and deletions may be made thereto, in addition to those expressly recited without departure from the spirit and scope of the invention as set forth in the following claims.

I claim:

1. A method of determining whether a urine specimen has been adulterated by a diuretic comprising the steps of:
    (a) measuring the specific gravity and creatinine concentration of the urine specimen,
    (b) calculating a normalized urine creatinine concentration as a function of the measured urine creatinine concentration and the measured urine specific gravity adjusted for the difference between the measured specific gravity and a referenced specific gravity for the substantially diuretic free population, and
    (c) comparing the calculated normalized urine creatinine concentration for the specimen tested with a range of expected normalized creatinine values for the substantially diuretic free population,
whereby if the normalized urine creatinine concentration is below the range of expected normalized creatinine values, the urine sample is rejectable as being adulterated.

2. The method of claim 1 wherein step (b) the normalized urine creatinine concentration is calculated in accordance with the following equation:

$$nu = u \cdot SGF$$

where nu is the normalized creatinine concentration, u is the measured creatinine concentration, SGF is the specific gravity factor of the urine sample expressed by the ratio (rsg−1)/(msg−1) where rsg is a preselected test reference specific gravity for the substantially diuretic free population and where msg is the measured specific gravity.

3. The method of claim 2 wherein step (c) the calculated normalized creatinine concentration is compared with the range of expected normalized creatinine values between 100 and 600 mg/dl.

4. The method of claim 3 wherein specific gravity is measured by a total solids test method.

5. The method of claim 4 wherein specific gravity is measured by refractometry.

6. A method for determining whether a urine specimen has been adulterated by the use of an osmotic diuretic comprising the steps of:
    (a) measuring the specific gravity of the urine specimen by an ionic strength method,
    (b) measuring the specific gravity of the urine specimen by a total solids method,
    (c) measuring the creatinine concentration of the urine sample,
    (d) calculating a normalized urine creatinine concentration as a function of the measured urine creatinine concentration and the larger of the values for specific gravities measured in steps (a) and (b), the larger specific gravity value being adjusted for the difference between the measured specific gravity and a reference specific gravity for a substantially diuretic free population, and
    (e) comparing the calculated normalized urine creatinine concentration for the specimen tested with a range of expected normalized creatinine values for the substantially diuretic-free population,
whereby if the normalized urine creatinine concentration is below the range of expected normalized creatinine values, the urine sample is rejectable as being adulterated by an osmotic diuretic.

7. The method of claim 6 wherein step (d) the normalized urine creatinine concentration is calculated in accordance with the following equation:

$$nu = u \cdot SGF$$

where nu is the normalized creatinine concentration, u is the measured creatinine concentration, SGF is the specific gravity factor of the urine sample expressed by the ratio (rsg−1)/(msg−1) where rsg is a preselected test reference specific gravity for the substantially diuretic free population and where msg is the measured specific gravity.

8. The method of claim 6 wherein step (e) the calculated normalized urine creatinine is compared with the range of expected normalized creatinine values between 100 and 600 mg/dl.

9. A method of determining whether a urine specimen has been adulterated by diuresis comprising the steps of:
    (a) measuring the specific gravity and creatinine concentration of the urine specimen,
    (b) calculating a normalized urine creatinine concentration as a function of the measured urine creatinine concentration and the measured urine specific gravity adjusted for the difference between the measured specific gravity and a referenced specific gravity for the substantially diuretic free population, (c) comparing the calculated normalized urine creatinine concentration for the specimen tested with a range of expected normalized creatinine values for the substantially diuretic-free population and with the measured urine creatinine concentration of the specimen for differences, whereby if the calculated normalized urine creatinine concentration is within the expected range of normalized creatinine concentrations and the value of the calculated normalized urine creatinine concentration is greater than the measured urine creatinine concentration, the urine sample is rejectable as being adulterated by diuresis.

10. The method of claim 9 wherein step (b) the normalized urine creatinine concentration is calculated in accordance with the following equation:

$$nu = u \cdot SGF$$

where nu is the normalized creatinine concentration, u is the measured creatinine concentration, SGF is the specific gravity factor of the urine sample expressed by the ratio (rsg−1)/(msg−1) where rsg is a preselected test reference specific gravity and where msg is the measured specific gravity.

* * * * *